(12) United States Patent
Rogers

(10) Patent No.: US 7,648,491 B2
(45) Date of Patent: Jan. 19, 2010

(54) MEDICAL SUBSTANCE TRANSFER SYSTEM

(76) Inventor: Bob Rogers, 5940 Pacific Mesa Ct., #205, San Diego, CA (US) 92121

( * ) Notice: Subject to any disclaimer, the term of this patent is extended or adjusted under 35 U.S.C. 154(b) by 133 days.

(21) Appl. No.: 11/435,274

(22) Filed: May 15, 2006

(65) Prior Publication Data

US 2006/0276770 A1 Dec. 7, 2006

Related U.S. Application Data

(60) Provisional application No. 60/681,083, filed on May 13, 2005, provisional application No. 60/685,193, filed on May 26, 2005, provisional application No. 60/724,638, filed on Oct. 7, 2005.

(51) Int. Cl.
*A61M 19/00* (2006.01)
(52) U.S. Cl. .................. 604/414; 604/415; 604/411
(58) Field of Classification Search ................ 604/403, 604/411, 412, 414, 415, 264, 256
See application file for complete search history.

(56) References Cited

U.S. PATENT DOCUMENTS

| | | | |
|---|---|---|---|
| 3,986,508 A | 10/1976 | Barrington | |
| 4,121,585 A | 10/1978 | Becker, Jr. | |
| 4,334,551 A | 6/1982 | Pfister | |
| 4,436,519 A | 3/1984 | O'Neill | |
| 4,564,054 A | 1/1986 | Gustavsson | |
| 4,610,469 A | 9/1986 | Wolff-Mooij | |
| 4,673,404 A | 6/1987 | Gustavsson | |
| 4,895,346 A | 1/1990 | Steigerwald | |
| 4,960,412 A | 10/1990 | Fink | |
| 5,064,416 A | 11/1991 | Newgard et al. | |
| 5,092,857 A | 3/1992 | Fleischhacker | |
| 5,100,394 A | 3/1992 | Dudar et al. | |
| 5,122,123 A | 6/1992 | Vaillancourt | |
| 5,167,648 A | 12/1992 | Jepson et al. | |
| 5,215,538 A | 6/1993 | Larkin | |

(Continued)

FOREIGN PATENT DOCUMENTS

EP 0 126 718 11/1984

(Continued)

OTHER PUBLICATIONS

"Baxa Corporation Introduces PhaSeal®, The Only Closed System for Safe Handling of Hazardous Drugs," PRWeb™ Press Release Newswire http://www.prweb.com/ , 2 pages, (Jun. 2003).

(Continued)

*Primary Examiner*—Leslie R Deak
(74) *Attorney, Agent, or Firm*—Fred C. Hernandez; Mintz, Levin, Cohn, Ferris, Glovsky and Popeo P.C.

(57) ABSTRACT

Disclosed is a fluid transfer system for transferring a substance from one vessel to another vessel while avoiding leakage of liquid and gas contaminants. The transfer system includes a needle safe design that is facilitated by a housing that shrouds a tip of a fluid transfer cannula such that the cannula tip is not exposed for inadvertent puncture. This feature may also be enhanced by use of a blunt tipped cannula. The fluid transfer system permits multiple access by enabling the easy swabbing of a septum prior to use.

11 Claims, 8 Drawing Sheets

U.S. PATENT DOCUMENTS

| | | |
|---|---|---|
| 5,269,771 A | 12/1993 | Thomas et al. |
| 5,340,359 A | 8/1994 | Segura Badia |
| 5,470,319 A | 11/1995 | Mayer |
| 5,492,147 A | 2/1996 | Challender et al. |
| 5,549,577 A | 8/1996 | Siegel et al. |
| 5,552,118 A | 9/1996 | Mayer |
| 5,597,536 A | 1/1997 | Mayer |
| 5,616,129 A | 4/1997 | Mayer |
| 5,616,130 A | 4/1997 | Mayer |
| 5,676,346 A | 10/1997 | Leinsing |
| 5,685,866 A | 11/1997 | Lopez |
| 5,694,686 A | 12/1997 | Lopez |
| 5,695,466 A | 12/1997 | Lopez et al. |
| 5,700,248 A | 12/1997 | Lopez |
| 5,738,663 A | 4/1998 | Lopez |
| 5,788,215 A | 8/1998 | Ryan |
| 5,788,675 A | 8/1998 | Mayer |
| 5,820,601 A | 10/1998 | Mayer |
| 5,820,614 A | 10/1998 | Erskine et al. |
| 5,833,213 A | 11/1998 | Ryan |
| 5,836,923 A | 11/1998 | Mayer |
| 5,839,715 A | 11/1998 | Leinsing |
| 5,848,997 A | 12/1998 | Erskine et al. |
| 5,873,862 A | 2/1999 | Lopez |
| 5,891,096 A | 4/1999 | Hyun et al. |
| 5,901,942 A | 5/1999 | Lopez |
| 5,928,204 A | 7/1999 | Lopez |
| 5,954,313 A | 9/1999 | Ryan |
| 5,971,965 A | 10/1999 | Mayer |
| 6,019,748 A | 2/2000 | Lopez |
| 6,048,335 A | 4/2000 | Mayer |
| 6,113,068 A | 9/2000 | Ryan |
| 6,132,403 A | 10/2000 | Lopez |
| 6,132,404 A | 10/2000 | Lopez |
| 6,142,446 A | 11/2000 | Leinsing |
| 6,152,900 A | 11/2000 | Mayer |
| 6,177,037 B1 | 1/2001 | Mayer |
| 6,183,448 B1 | 2/2001 | Mayer |
| 6,206,861 B1 | 3/2001 | Mayer |
| 6,210,624 B1 | 4/2001 | Mayer |
| 6,261,268 B1 | 7/2001 | Mayer |
| 6,299,131 B1 | 10/2001 | Ryan |
| 6,325,782 B1 | 12/2001 | Lopez |
| 6,428,520 B1 | 8/2002 | Lopez et al. |
| 6,572,591 B2 | 6/2003 | Mayer |
| 6,572,592 B1 | 6/2003 | Lopez |
| 6,635,044 B2 | 10/2003 | Lopez |
| 6,669,673 B2 | 12/2003 | Lopez |
| 6,669,681 B2 | 12/2003 | Jepson et al. |
| 6,682,509 B2 | 1/2004 | Lopez |
| 6,695,817 B1 | 2/2004 | Fangrow, Jr. |
| 6,706,022 B1 | 3/2004 | Leinsing et al. |
| 6,745,998 B2 | 6/2004 | Doyle |
| 6,758,833 B2 | 7/2004 | Lopez |
| 6,802,490 B2 | 10/2004 | Leinsing et al. |
| 6,840,501 B2 | 1/2005 | Doyle |
| 6,875,205 B2 | 4/2005 | Leinsing |
| 2002/0032433 A1 | 3/2002 | Lopez |
| 2002/0040207 A1 | 4/2002 | Lopez |
| 2002/0138047 A1 | 9/2002 | Lopez |
| 2002/0143301 A1 | 10/2002 | Lopez |
| 2002/0147431 A1 | 10/2002 | Lopez et al. |
| 2003/0032940 A1 | 2/2003 | Doyle |
| 2003/0136932 A1 | 7/2003 | Doyle |
| 2003/0187420 A1 | 10/2003 | Akerlund et al. |
| 2004/0002684 A1 | 1/2004 | Lopez |
| 2004/0034325 A1 | 2/2004 | Lopez |
| 2004/0073174 A1 | 4/2004 | Lopez |
| 2004/0176867 A1 | 9/2004 | Lopez |
| 2004/0217315 A1 | 11/2004 | Doyle |
| 2004/0227120 A1 | 11/2004 | Raybuck |
| 2004/0243070 A1 | 12/2004 | Lopez |
| 2004/0249235 A1 | 12/2004 | Connell et al. |

FOREIGN PATENT DOCUMENTS

| | | |
|---|---|---|
| WO | 84/04672 | 12/1984 |
| WO | 84/04673 | 12/1984 |

OTHER PUBLICATIONS

"PhaSeal® Protects those who care," http://www.phaseal.com/siteUS/default.asp, 10 pages, (Webpages accessed Mar. 30, 2005).

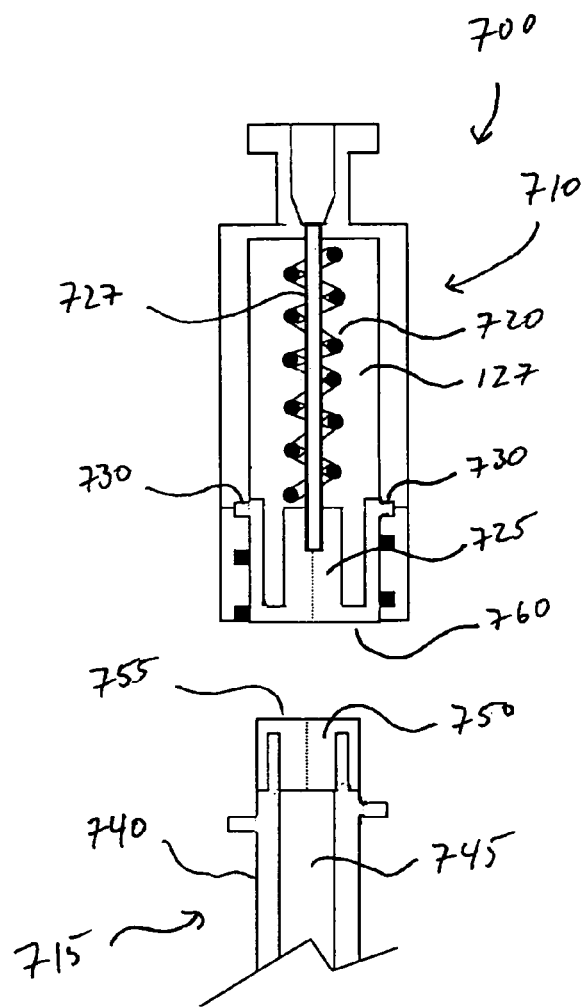
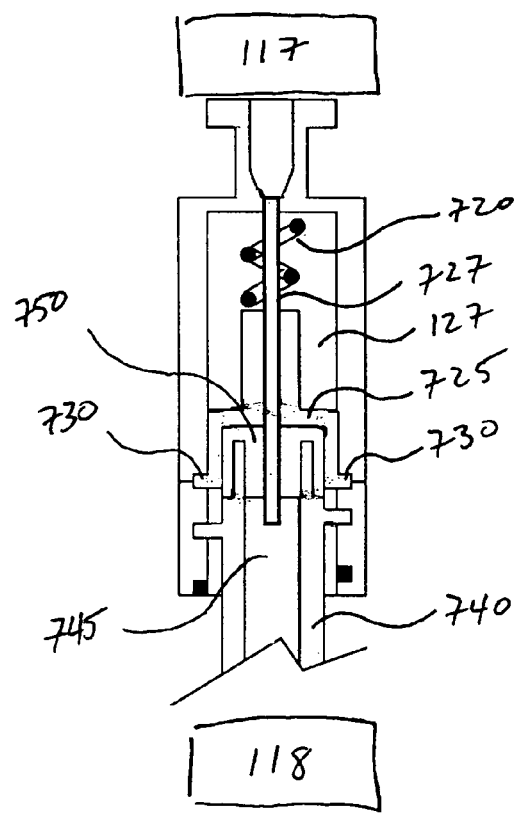
FIGURE 7
FIGURE 8

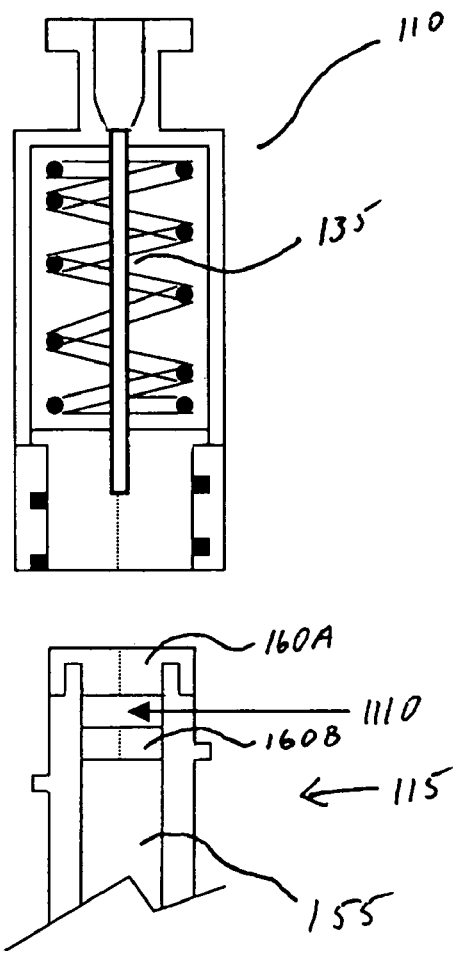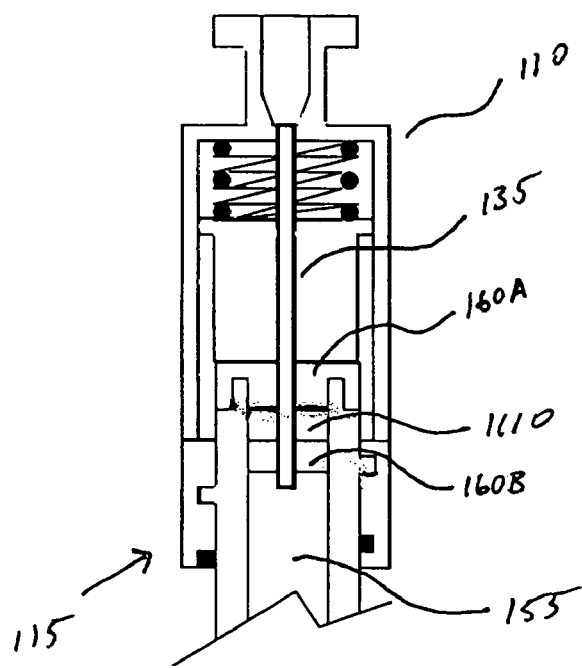
FIGURE 11
FIGURE 12

MEDICAL SUBSTANCE TRANSFER SYSTEM

REFERENCE TO PRIORITY DOCUMENTS

This application claims priority of the following co-pending U.S. Provisional Patent Applications: (1) U.S. Provisional Patent Application Ser. No. 60/681,083 entitled "Medical Substance Transfer System", filed May 13, 2005; (2) U.S. Provisional Patent Application Ser. No. 60/685,193 entitled "Medical Substance Transfer System", filed May 26, 2005; and (3) U.S. Provisional Patent Application Ser. No. 60/724,638 entitled "Medical Substance Transfer System", filed Oct. 7, 2005. Priority of the aforementioned filing dates is hereby claimed, and the disclosure of the Provisional Patent Application is hereby incorporated by reference in their entirety.

BACKGROUND

The present disclosure relates to a needle-stick safe fluid transfer system for preventing inadvertent exposure to chemicals or drugs or aerosolized components of the same. More particularly, the present disclosure relates to a means of connecting two separate devices to enable bi-directional fluid flow without the unintended exposure or risk of puncture.

Pharmaceuticals and chemicals (i.e. antineoplastics, cytotoxins, antivirals, antibiotics and radio-pharmaceuticals) are quite beneficial in the treatment of disease. However, they may cause problems for the healthcare personnel handling them. The drugs can be quite dangerous and caustic. Thus, in the preparation and administration of drugs intended for injection or infusion, special considerations must be made for safety. Inadvertent and unintended exposure can lead to serious consequences.

Aerosolization of these drugs during the preparation phase is well documented. Studies have shown residual drug to be found on work surfaces, trays, floors, vials, and outside those areas where preparation is performed. During the administration phase it is not uncommon for personnel to come into contact with these drugs through spills, inadvertent contact and residual drug remaining on surfaces. Furthermore, studies have shown the presence of these drugs in the urine of healthcare personnel. Serious complications can occur due to exposure. Such complications include liver damage, leukemia, non-Hodgkins lymphoma, skin cancer, miscarriages, malformation and low birth weight.

In view of the foregoing, there is a need for improved fluid transfer systems that prevent inadvertent exposure to harmful materials, such as chemicals or drugs or aerosolized components of such drugs.

SUMMARY

Disclosed is a fluid transfer system for transferring a substance from one vessel to another vessel while avoiding leakage of liquid and gas contaminants. The transfer system includes a needle safe design that is facilitated by a housing that shrouds a tip of a fluid transfer cannula such that the cannula tip is not exposed for inadvertent puncture. This feature may also be enhanced by use of a blunt tipped cannula. The fluid transfer system permits multiple access by enabling the easy swabbing of a septum prior to use.

In one embodiment, the medical substance transfer system includes a transfer device and a receiver device adapted to removably couple to the transfer device. The transfer device can include, for example, at least the following: (1) a transfer housing defining an interior chamber; (2) a first septum movably disposed in a distal end of the chamber in a sealing relationship with the chamber, wherein the first septum has a distal surface substantially flush with a distal edge of the transfer housing; (3) a cannula that extends through the chamber such that when the transfer device is uncoupled from the receiver device, a distal tip of the cannula is optionally positioned proximal of the distal edge of the transfer housing; and (4) a biasing member inside the chamber, the biasing member adapted to bias the first septum toward the distal end of the chamber.

The receiver device can include, for example: (1) a receiver housing that defines an interior passageway in communication with a distal tip of the cannula when the transfer device and receiver device are coupled to one another; and (2) a second septum disposed in a proximal region of the housing. The second septum can have a proximal surface substantially flush with a proximal edge of the housing such that the proximal surface of the second septum is in juxtaposed contact with the distal surface of the first septum when the transfer device and receiver device are coupled to one another. The second septum provides a barrier to prevent fluid from escaping from the interior passageway of the receiver housing.

The medical substance transfer system can further include a wiping member disposed in the housing distal of the second septum. The wiping member is adapted to wipe the cannula during uncoupling of the receiver device and transfer device. The second septum and the wiping member can define a repository, such as a space, therebetween. The repository is adapted to retain fluid. The wiping member can comprise any of a variety of structures, such as a third septum or a duckbill valve.

The first and second septums optionally contact the cannula when the transfer device and receiver device are coupled to one another such that the first and second septums wipe the cannula during coupling and uncoupling of the transfer and receiver devices. The first septum, second septum, and the wiping member can all wipe the cannula during uncoupling of the transfer device from the receiver device.

In one embodiment, the distal tip cannula is at least partially positioned inside the first septum when the transfer device and receiver device are uncoupled from one another.

The first and second septums and any wiping members may optionally have slits for passage of the cannula therethrough. In addition, the first and second septums can comprise resilient material that provides bulk resilience to maintain a closed, default state. The distal tip of the cannula can be blunt or sharpened.

In one embodiment, at least a portion of the first septum moves in a proximal direction through the interior chamber of transfer housing during coupling of the receiver device to the transfer device. The first septum maintains a sealed relationship with the chamber during such movement.

The transfer device is configured to attach to a first vessel such that the cannula fluidly communicates with the first vessel. The receiver device attaches to a second vessel such that the interior passageway of the receiver housing communicates with the second vessel. Upon connection of the transfer device to the receiver device, the cannula and interior passageway can collectively provide a passageway between the first and second vessels. The first septum and the biasing member can be separate devices or can be combined into a single device.

BRIEF DESCRIPTION OF THE DRAWINGS

FIGS. 7 and 8 show an alternative embodiment of the transfer system.

FIGS. 11 and 12 show yet another embodiment of the transfer system.

DETAILED DESCRIPTION

Disclosed is a transfer system that can be used to transfer a substance between a pair of vessels in a manner that avoids contamination.

Figure 1:
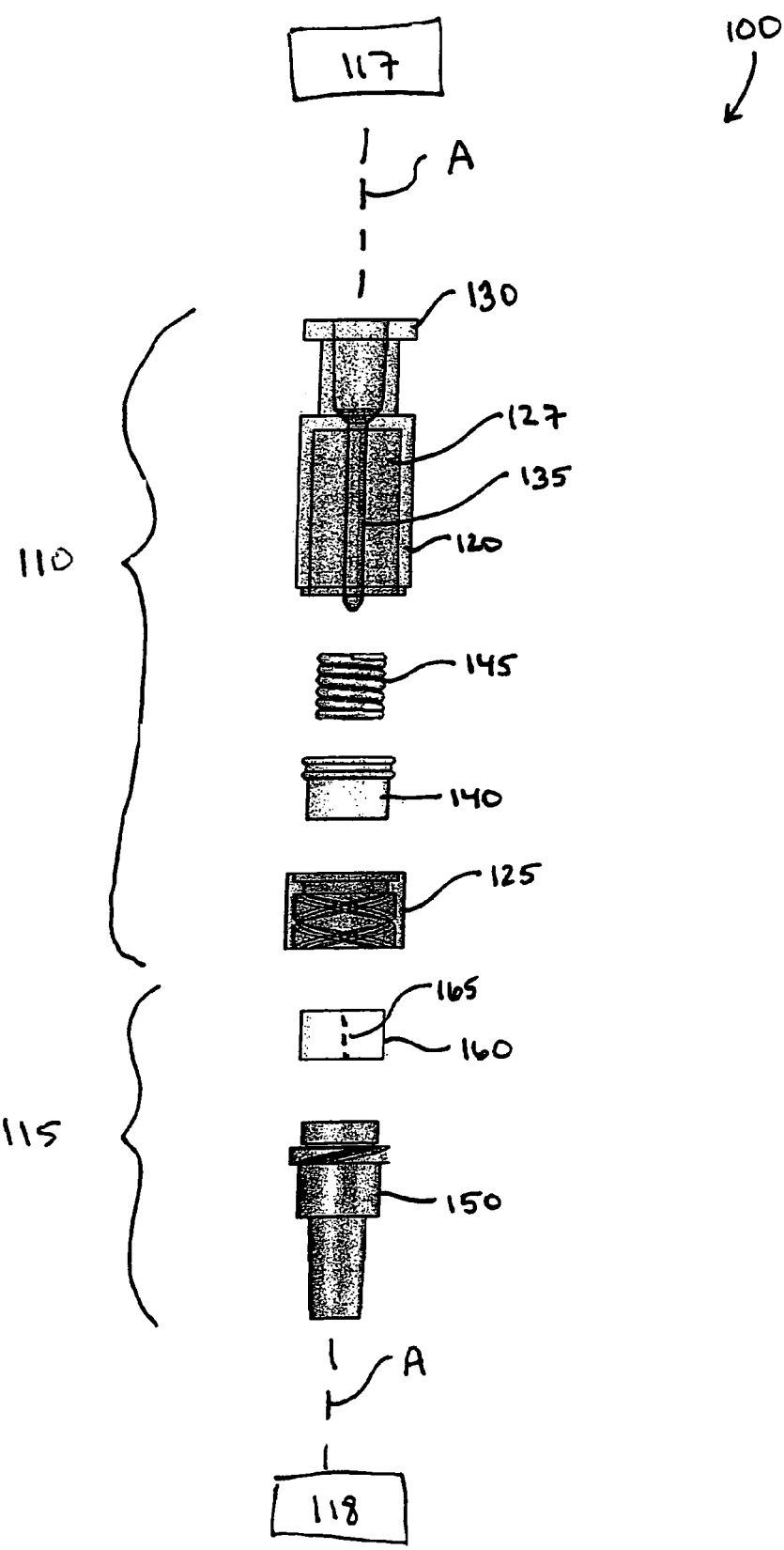
FIG. 1 shows an exploded, partial cross-sectional view of a first embodiment of the transfer system.

FIG. 1 shows an exploded, partial cross-sectional view of a first embodiment of the transfer system 100, which includes a transfer device 110 and a receiver device 115. The transfer device 110 and the receiver device 115 are configured to be removably coupled to one another for transferring a substance therebetween.

In this regard, the transfer device 110 is described herein as the device from which the substance is transferred and the receiver device 115 is described as the device for which the substance is transferred to. It should be appreciated, however, that the transfer device 110 can be configured to receive the substance from the receiver device 115 such that the transfer device 110 is the receiving member and the receiver device 115 is the transfer member. For example, the cannula-based housing described below can be on the receiving side of the substance. Thus, the nomenclature of "transfer" and "receiver" are used in an exemplary manner and are not to be considered limiting. Furthermore, the transfer system 110 can also be used for bi-directional transfer of the substance across the system such that each device 110 and 115 can be both a transfer device and a receiver device.

Figure 2:
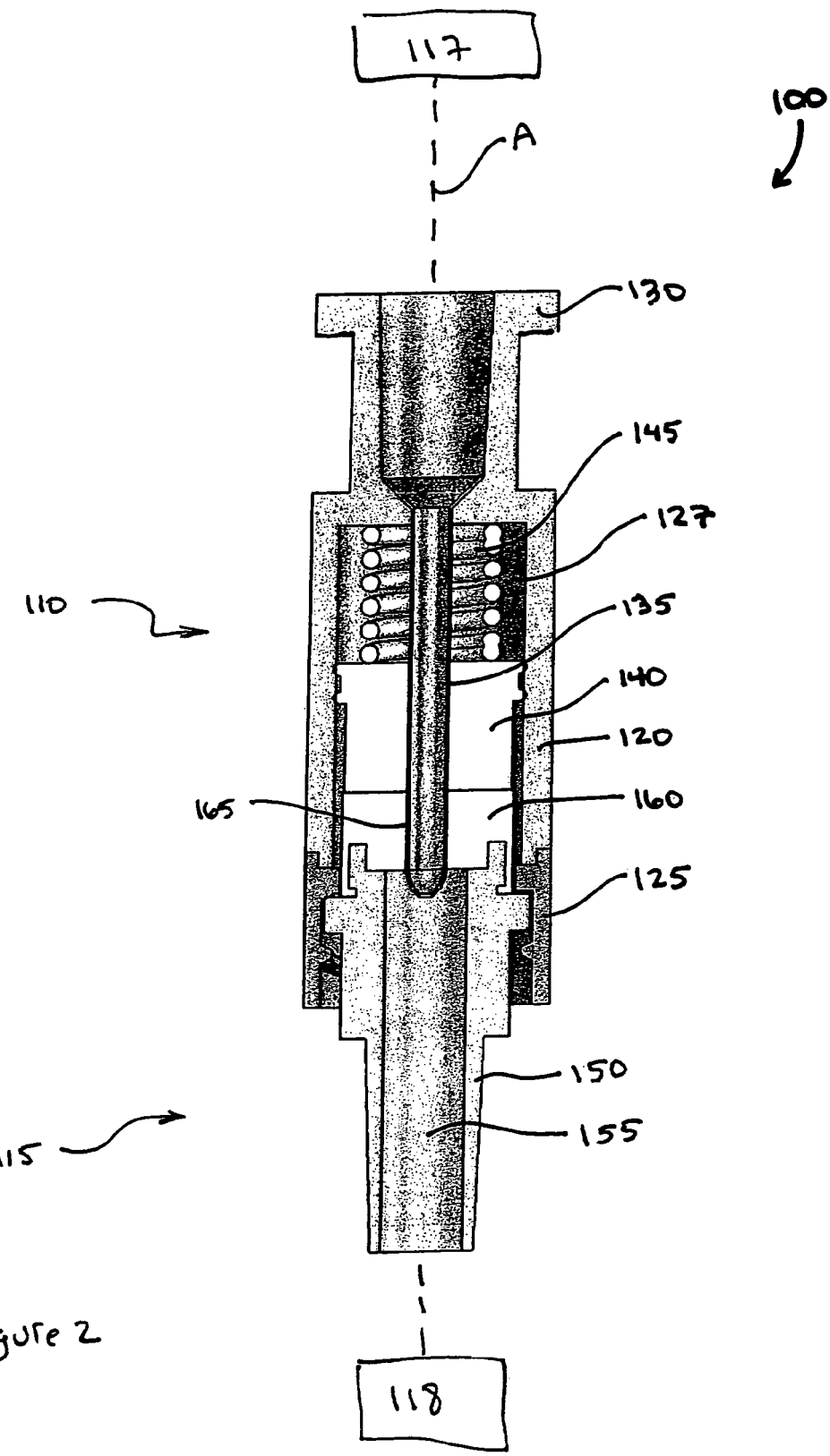
FIG. 2 shows a cross-sectional view of the transfer system in an assembled state with a transfer device and a receiver device coupled to one another.

FIG. 2 shows a cross-sectional view of the transfer system 100 in an assembled state with the transfer device 110 and the receiver device 115 coupled to one another.

The transfer system 100 is configured to transfer any of a variety of substances, including, but not limited to, medical fluids, drugs and body fluids including blood, from a first vessel 117 to a second vessel 118. As mentioned, the transfer system 100 can also be configured to transfer the substance from the second vessel 118 to the first vessel 117. For example, in the case of blood, the transfer system 100 can transfer blood from a vessel 118 comprised of a catheter in a patient to a vessel 117 comprised of a syringe. The first vessel 117 and the second vessel 118 are both schematically represented using boxes labeled 117 and 118 in FIGS. 1 and 2. Thus, the vessels 117 and 118 can be any type of container configured to permanently or temporarily hold, store, or transfer a fluid substance. The first and second vessels 117 and 118 can each comprise, for example, an injection syringe, a blood collection container, an ampoule, a drug container, a drug vial adapter, a solution container, an injection port, a needle free valve, a y-connector, a catheter, any portion of an infusion or intravenous injection system, a blood vessel of a patient, etc.

The transfer device 110 is configured to be removably attached at a proximal end to the first vessel 117 and the receiver device 115 is configured to be removably attached at a distal end to the second vessel 118. Alternately, the first vessel 117 can be fixedly attached to the transfer device 110 and the second vessel 118 fixedly attached to the receiver device 115. In any event, the transfer system 100 facilitates the transfer of a substance from the first vessel 117 to the second vessel 118 in a manner that avoids contamination and reduces the likelihood of the substance or gases emanating from said substance escaping into the environment. It should be appreciated that the terms "proximal" and "distal" are relative terms and should not be considered as limiting to the device.

With reference to FIGS. 1 and 2, the transfer device 110 includes a proximal housing 120 and a distal housing 125 that can be attached to one another to collectively form an outer housing for the transfer device 110. The proximal housing 120 and distal housing 125 collectively form an internal chamber 127 that is peripherally enclosed by walls of the outer housing. A coupler component 130 is disposed on a proximal end of the proximal housing 120 for enabling the transfer device 110 to be fluidly coupled to the first vessel 117, as described more fully below. A cannula 135 having a blunt distal tip extends through the internal chamber 127 along a central, longitudinal axis A of the transfer system 100. It should be appreciated that the blunt distal tipped cannula 135 can also be a sharply pointed cannula. A transfer septum 140 is movably positioned within the internal chamber 127. The transfer septum is designed to keep the contents of the internal chamber 127 from escaping outside the internal chamber 127. For example, if the substance leaks or is otherwise disposed in the internal chamber 127, the transfer septum 140 provides a seal with the walls of the internal chamber 127 to prevent the substance from escaping into the surrounding environment.

A biasing member 145, such as a spring, is disposed in the internal chamber 127 between the transfer septum 140 and a portion of the proximal housing 120, such as a proximal wall of the proximal housing 120. The biasing member 145 biases the transfer septum 140 toward a default position, such as at or near a distal end of the internal chamber 127. The biasing member 145 is shown in FIGS. 1 and 2 as a spring, but it should be appreciated that the biasing member 145 can be any structure or mechanism that provides a biasing force against the transfer septum 140.

With reference still to FIGS. 1 and 2, the receiver device 115 includes a housing 150. As shown in FIG. 2, the housing 150 defines an internal passageway 155 for the passage of fluid received via the transfer device 110 into the second vessel 118. The receiver device 115 further includes a receiver septum 160 disposed at a proximal end of the housing 150 in the pathway of the passageway 155. The receiver septum 160 maintains an enclosure of housing 150 and passageway 155 such that the contents of passageway 155 cannot exit or otherwise escape from housing 150 except by means of the cannula 135 passing through the receiver septum 160. A slit 165 extends longitudinally through the receiver septum 160 along the axis A. The slit 165 can be manufactured such that slit 165 remains closed in a default state to prevent the flow of fluid therethrough unless the slit 165 is manually opened. In this regard, the receiver septum 160 can be manufactured of a polymeric and resilient material that is able to provide bulk resilience to maintain the closed, natural state of the slit 165. The slit 165 can be manually opened by inserting the cannula 135 of the transfer device 110 through the slit 165 upon coupling of the transfer device and the receiver device. In this manner, the cannula 135 provides a fluid pathway between the transfer device 110 and the receiver device 115, as described more fully below. It should be appreciated that should cannula 135 be sharply tipped, a pre-formed slit 165 in receiver septum 160 may not be a required element.

The transfer device 110 is now described in more detail with reference to FIG. 3, which shows a cross-sectional view of the transfer device 110. The coupler component 130 comprises any type of mechanism that can be coupled to the first vessel 117. In one embodiment, the coupler component 130 is a female Luer lock, female Luer slip type or other form designed for the removable attachment of first vessel 117. The coupler component 130 could also be configured as a male Luer lock, male Luer slip connector, or other form designed for the removable attachment of first vessel 117. For non-removable connections the coupler could be an integrally molded part of another device or attached by bonding, welding or other means to fixedly attach two parts.

An entry chamber 305 is disposed within the proximal end of the proximal housing 120 and communicates with the first vessel 117 (shown in FIGS. 1 and 2) when attached to the transfer device 110, such as via a syringe that is disposed in the entry chamber upon coupling to the first vessel 117. The entry chamber 305 also communicates with a transfer passageway 310 that extends axially through the cannula 135. The transfer passageway 310 communicates with an aperture 307 at the distal end of the cannula 135 for transfer of fluid out of the cannula 135.

Figure 3:
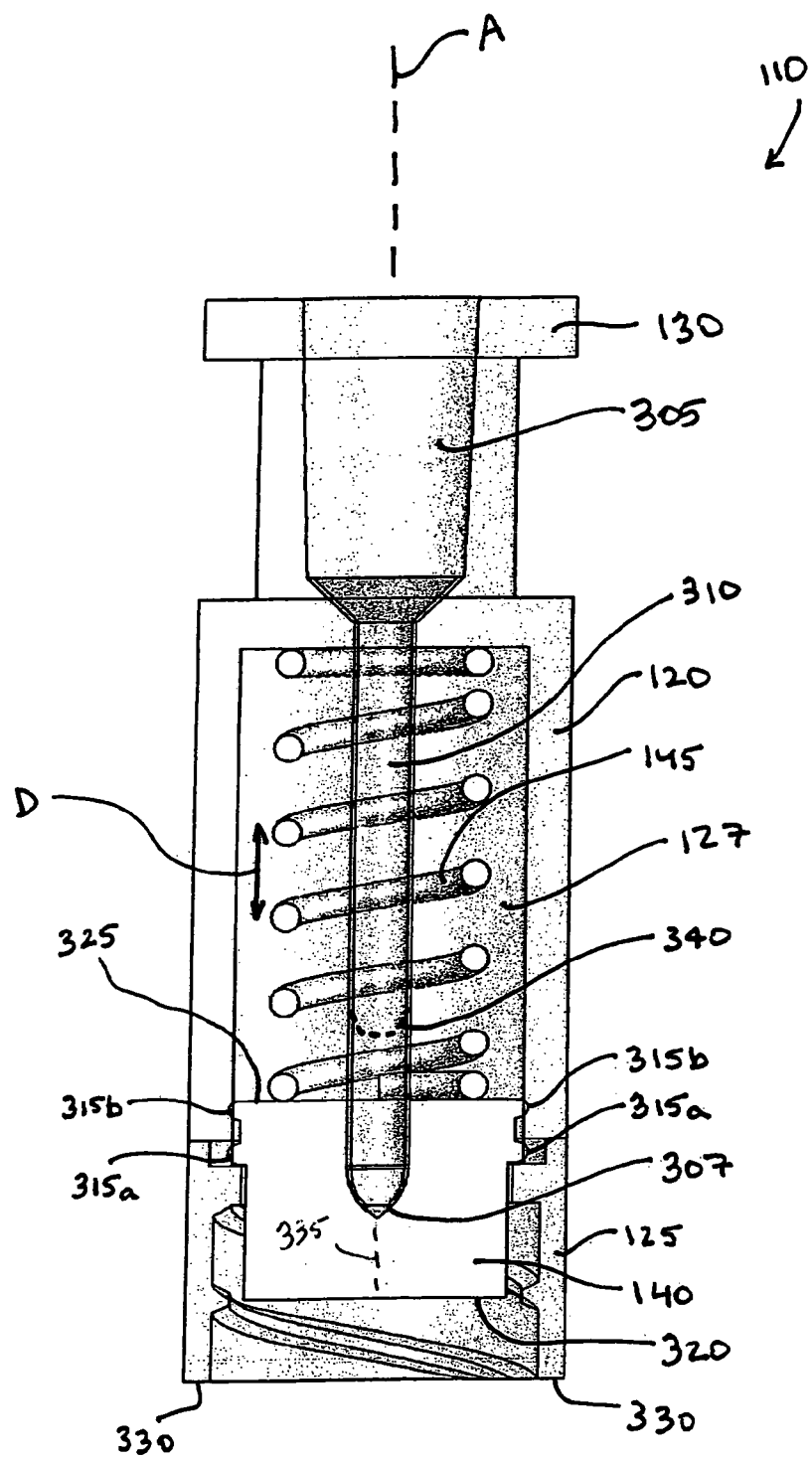
FIG. 3 shows a cross-sectional view of the transfer device.

With reference still to FIG. 3, the transfer septum 140 is movably disposed within the internal chamber 127. The transfer septum 140 is configured to slidably move within the internal chamber 127 along the directions represented by the arrows D in FIG. 3. The biasing member 145 biases the transfer septum 140 toward a distal-most position within the internal chamber 127 such that the transfer septum 140 is in a distal-most position as a default position.

The transfer septum 140 includes one or more sealing portions that sealingly engage the internal walls of the chamber 127. The structural configuration of the sealing portions can vary. In one embodiment, the sealing portions comprise annular protrusions 315 peripherally located on the transfer septum 140. The protrusions 315 can serve a variety of purposes. For example, the distal-most protrusion 315a functions as a mechanical stop that engages a shoulder on the housing to prevent the transfer septum 140 from being expelled out of the housing of the transfer device 110. The protrusions 315 can also function as o-ring type seals that sealingly engage an internal wall of the internal chamber 127 to prevent fluid (liquid or gas) from escaping from the internal chamber 127. Thus, the protrusions 315 form a fluid-proof seal that prevents fluid from escaping from the internal chamber 127.

With reference still to FIG. 3, the transfer septum 140 has a distal surface 320 and a proximal surface 325. In one embodiment, the transfer septum 140 has a size and position such that there is a space between the distal surface 320 and a distal end 330 of the transfer device housing, as is shown in FIG. 3. However, it should be appreciated that the distal surface 320 of the transfer septum 140 can be positioned flush with the distal end 330 of the transfer device housing or can at least partially or entirely protrude distally outward from the transfer device housing. The distal surface 320 can vary in contour. For example, the distal surface 320 can be flat or it can be convex such that the surface bows outward in a distal direction.

With reference still to FIG. 3, a slit 335 extends longitudinally through the transfer septum 140 along the axis A in the same manner as the slit 165 in the receiver septum 160. The transfer septum 140 can be manufactured of a polymeric and resilient material that provides bulk resilience to maintain a natural, closed state of the slit 335. The slit 335 can be penetrated by the cannula 135. In one embodiment, a distal region of the cannula 335 is positioned within the slit 335 when the transfer septum is in the default position, as shown in FIG. 3. That is, the cannula penetrates the slit 335 when the transfer septum 140 is in the default position. In an alternate embodiment, the distal region of the cannula 135 is positioned outside of the transfer septum 140 when the transfer septum 140 is in the default position. Thus, in the alternate embodiment, the distal tip (represented by lines 340 in FIG. 3) of the cannula 135 does not penetrate the slit 335. It should be appreciated that should cannula 135 be sharply tipped a pre-formed slit 335 in transfer septum 140 may not be a required element.

The transfer of fluid out of the distal end of the transfer device 110 can be accomplished primarily through the connection of the transfer device 110 to a receiver device such as the receiver device 115. The two devices can mate via two complimentary luer fittings, e.g. the male luer of a syringe will mate to a female luer on a catheter, stopcock, needle-free valve etc. The luer is a standardized connector within the medical community. The specifications for a luer can be found in ANSI/HIMA MD70.1 and ISO 594 standards.

In one embodiment, the distal end of the transfer device housing has an internal diameter that is smaller than the outside diameter of a female luer in order to prevent or inhibit a female luer from being inserted into the distal end of the transfer device housing. A female luer is an open ended connector. Thus, if the transfer device housing was designed to accommodate the entry of the female luer, the internal chamber 127 could be opened to the atmosphere and fluid and gases within the chamber could be released to atmosphere. This is an undesirable result. The smaller (relative to a female luer) internal diameter of the transfer device housing prevents connection to a standard female luer.

In another embodiment, the proximal end of the receiver device 115 is generally a female luer that has been modified to include a septum that seals with the transfer device 110. In this way the transfer device housing can mate with the modified female luer to achieve the intended safe transfer of fluids.

The receiver device 115 is now described in more detail with reference to FIG. 4, which shows a cross-sectional view of the receiver device 115. As mentioned, the receiver device 115 includes a housing 150 and a receiver septum 160 mounted at a proximal end of the housing 150. The receiver septum 160 includes a slit 165 that is penetrated by the cannula 135 when the receiver device 115 is coupled to the transfer device 110, as described more fully below. The receiver septum 160 has a proximal surface 402 that can be flat, concave, or convex in shape.

An attachment structure 405 is located on the receiver device 115 for attaching to a corresponding structure on the transfer device 110. The attachment structure 405 can comprise any structure or mechanism for removably attaching a first component to a second component, such as threads, compression fit, a latching mechanism, etc.

Figure 4:
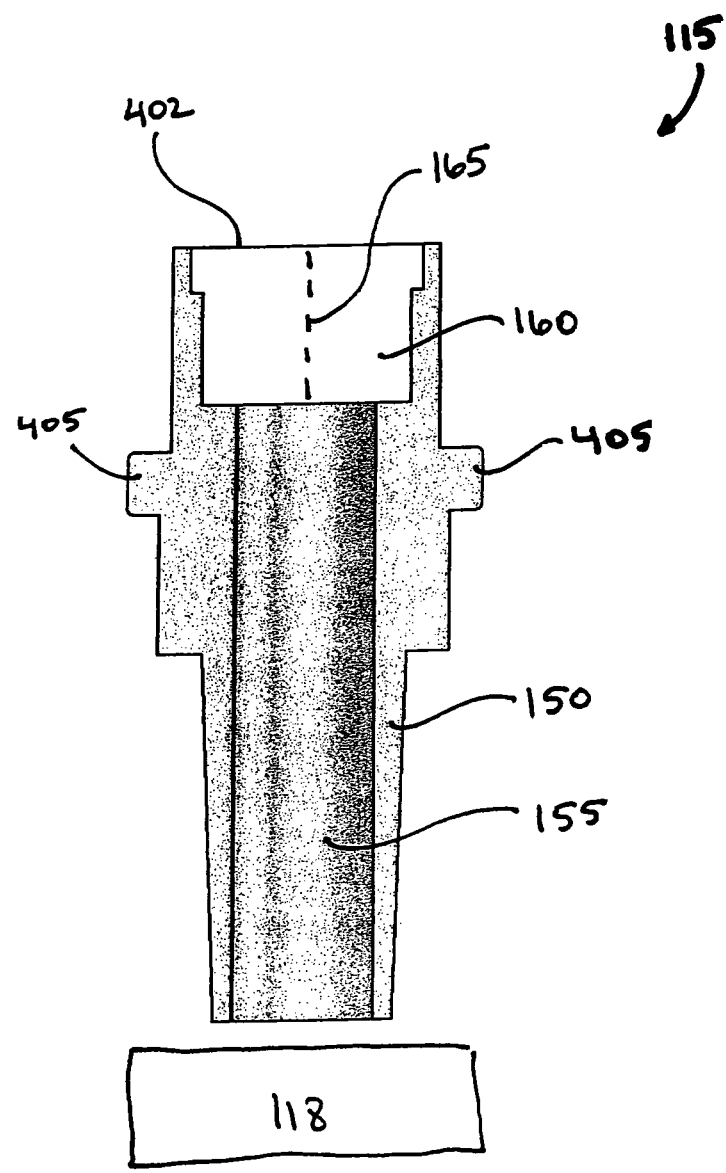
FIG. 4 shows a cross-sectional view of the receiver device.

With reference still to FIG. 4, the receiver device 115 can be coupled at a distal end to the second vessel 118. When coupled to the second vessel, the internal passageway 155 of the transfer device 115 communicates with the second vessel 118.

Figure 5:
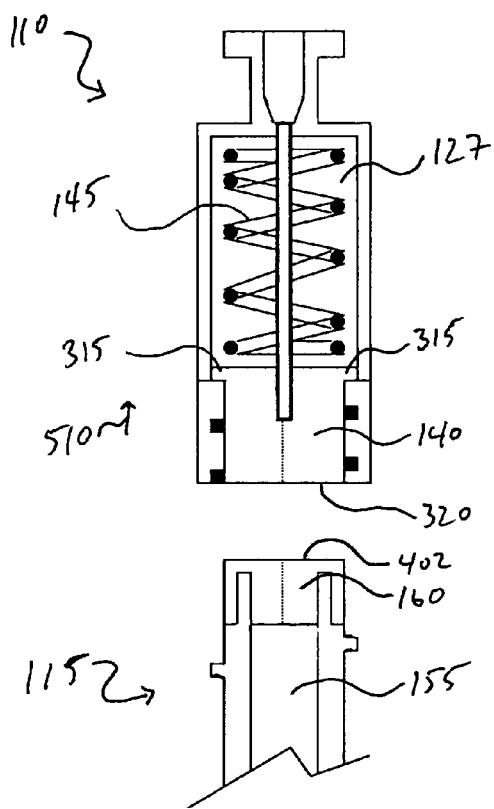
FIG. 5 shows the transfer device positioned adjacent the receiver device just prior to coupling of the two devices.

The operation of the transfer system 100 is now described with reference to FIGS. 5 and 6, which show schematic representations of the transfer device 110 and the receiver device 115. FIG. 5 shows the transfer device 110 positioned adjacent the receiver device 115 just prior to coupling of the two devices. Prior to coupling the devices, the biasing member 145 maintains the transfer septum 140 in its default distal-most position.

The transfer device 110 and receiver device 115 are coupled to one another as follows. The receiver device 115 is first oriented such that the distal surface 320 of the transfer septum 140 faces the proximal surface 402 of the receiver septum 160, as shown in FIG. 5. The receiver device 115 is moved toward the transfer device 110 (as represented by the arrow 510 in FIG. 5) such that the proximal surface 402 of the receiver septum 160 abuts the distal surface 320 of the transfer septum 140. Thus, the proximal surface 402 and the distal surface 320 are in juxtaposed contact with one another.

Figure 6:
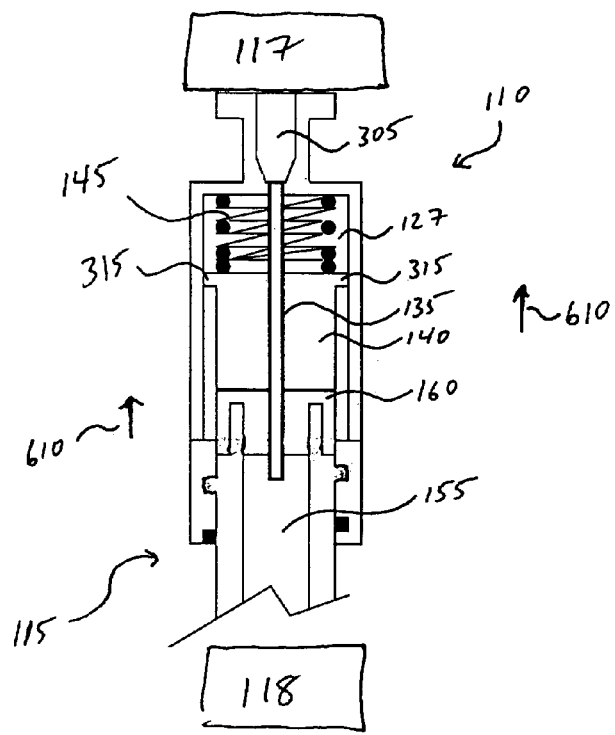
FIG. 6 shows the transfer device coupled to the receiver device.

With reference now to FIG. 6, the receiver device 115 is then moved into the transfer device 110 (as represented by the arrows 610 in FIG. 6) such that the receiver septum 160 pushes the transfer septum 140 in the directions of the arrows 610. A sufficient force is exerted against the transfer septum 140 to overcome the biasing force exerted by the biasing member 145 and thereby slide the transfer septum 140 upward (with respect to FIG. 6) into the internal cavity 127 of the transfer device 110. As the transfer septum 140 moves upward, the distal surface 320 of the transfer septum 140 moves upwardly past the distal tip of the cannula 135. The cannula 135 penetrates the slit in the receiver septum 160 until the distal tip of the cannula 135 communicates with the transfer passageway 155 in the receiver device 115, as shown in FIG. 6. In this manner, the cannula 135 provides a fluid passageway between the entry chamber 305 of the transfer device 110 and the internal passageway 155 of the receiver device 115. It should be noted that, in this embodiment, as the transfer septum 140 moves upward, the protrusions 315 slide along the inner walls of chamber 127 and they form a compression sliding seal to continuously maintain a sealed internal chamber 127.

As shown schematically in FIG. 6, the first vessel 117 is coupled to the transfer device 110 and the second vessel 118 is coupled to the receiver device 115. As mentioned, the first vessel 117 communicates with the entry chamber 305 of the transfer device 110 and the second vessel 118 communicates with the internal passageway 155 of the receiver device 115. The fluid substance is transferred from the first vessel 117, into the entry chamber 305, through the cannula 135, into the internal passageway 155, and into the second vessel 118. During such transfer, the transfer septum 140 and the receiver septum 160 remain in juxtaposed contact with one another.

An alternative embodiment of the transfer system, referred to as transfer system 700, is now described with reference to FIGS. 7 and 8. The transfer system 700 includes a transfer device 710 and a receiver device 715. The transfer device 710 includes an outer housing similar to the outer housing of the previous embodiment. A biasing member 720 exerts a biasing force against a transfer septum 725 to maintain the transfer septum 725 in a default state. The transfer septum 725 includes a slit that can be passed through by a cannula 727 of the transfer device 710. An attachment region 730 of the transfer septum 725 is fixedly attached to the outer housing of the transfer device 110 in a sealing manner. That is, the attachment region 730 provides a fluid-tight seal between the transfer septum 725 and the outer housing of the transfer device 110. In this manner, a sealed chamber 127 is located within the outer housing proximal of the transfer septum 725.

With reference still to FIGS. 7 and 8, the receiver device 715 includes a housing 740 that defines an internal passageway 745. A receiver septum 750 is attached to the housing 740 and includes a slit that can be passed through by the cannula 727 when the transfer device 710 and the receiver device 715 are coupled to one another. As can be appreciated from the previous embodiment, the transfer septum 725 and the receiver septum 750 need not be slit if the cannula 727 has a sharp tip.

In use, the receiver device 715 is inserted into the transfer device 710 such that a proximal surface 755 of the receiver septum 750 abuts a distal surface 760 of the transfer septum 725. The receiver septum 750 exerts a force against the transfer septum 725 to overcome the force exerted by the biasing member 720 and push the transfer septum 725 upward (relative to FIG. 7) into the housing of the transfer device 710.

As mentioned, the attachment region 730 of the transfer septum 725 is fixedly attached to the housing of the transfer device 710. As the receiver device 715 pushes upward into the transfer device 710, at least a portion of the transfer septum 725 moves upwardly into the transfer device housing while the attachment region 730 of the transfer septum 725 remains fixed relative to the transfer housing, as best shown in FIG. 8. The attachment region 730 of the septum creates a sealed chamber 127 inside the housing to prevent the escape of any substance from the chamber into the environment. During this process, the distal surface 760 of the transfer septum 725 remains in juxtaposed contact with the proximal surface 755 of the receiver septum 750.

With the transfer device 710 and the receiver device 715 coupled to one another, the transfer system 700 can be used to transfer a substance from the first vessel 117 to the second vessel 118 via the cannula 727.

Figure 9:
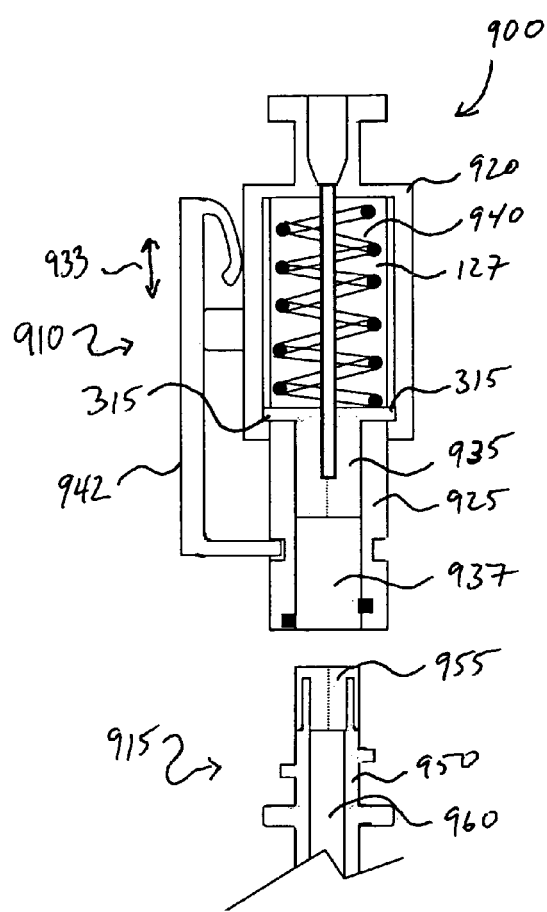
FIGS. 9 and 10 show yet another embodiment of the transfer system.
Figure 10:
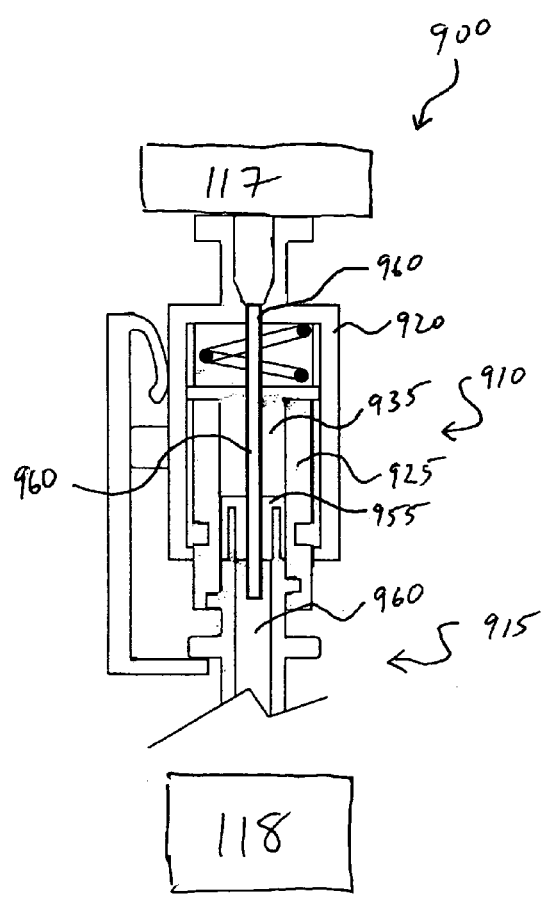

FIGS. 9 and 10 show yet another embodiment of the transfer system, referred to as the transfer system 900, which includes a transfer device 910 and a receiver device 915. The transfer device 910 includes a proximal housing 920 and a distal housing 925 that is slidably attached to the proximal housing 920. A transfer septum 935 is fixedly attached to the distal housing 925. A cavity 937 is located in the distal housing 925 just below the transfer septum 935 and is sized to receive at least a portion of the receiver device 915.

A biasing member 940 is positioned inside the proximal housing 920 and exerts a force against the transfer septum 935 to maintain the transfer septum 935 and the distal housing 925 in a default, distal position, as shown in FIG. 9. The transfer septum 935 and/or the distal housing 925 includes a shoulder or other structure that engages the proximal housing 920 to prevent the distal housing 925 and attached transfer septum 935 from being expelled from the proximal housing 920.

The distal housing 925 can slide relative to the proximal housing 920 along the directions represented by the arrows 933 in FIG. 9. A latching mechanism 942 is attached to the proximal housing 920. The latching mechanism 942 removably engages a portion of the distal housing 925 and provides a means of fixing the position of the distal housing 925 relative to the proximal housing 920 when sliding movement is not desired. The latching mechanism 942 can be disengaged to permit the distal housing 925 to slide relative to the proximal housing 920.

With reference still to FIGS. 9 and 10, the receiver device 915 includes a housing 950 and a receiver septum 955 as in the previous embodiments. An internal passageway 960 is contained in the housing 950.

In use, receiver device 915 is inserted into the cavity 937 of the transfer device 937 until the receiver septum 955 is in juxtaposed contact with the transfer septum 935. The latching mechanism 942 is released and the receiver device 915 is pushed upwardly (relative to FIG. 9) into the transfer device 910 to force the distal housing 925 and attached transfer septum 935 to overcome the biasing force of spring 940 to slide upwardly relative to the proximal housing 920, as shown in FIG. 10. During this process, the transfer septum 935 and the receiver septum 955 remain in juxtaposed contact with one another. The cannula 960 passes through the slits in both septums and provides a fluid passageway between the first vessel 117 and the second vessel 118, which are attached to the transfer device 910 and the receiver device 915, respectively. As can be appreciated from the prior embodiments the transfer septum 935 and the receiver septum 955 need not be slit if the cannula 960 has a sharp tip.

FIGS. 11 and 12 show another embodiment of the transfer system 100 in which the receiver device 115 includes first and second seals or septums 160a and 160b, respectively. The first septum 160a is positioned at or near a proximal edge of the receiver device 115 and can include a slit as in the previous embodiments. The second septum 160b is positioned distally of the first septum 160b such that an air space 1110 is interposed between the first and second septums.

The first and second septums are configured and positioned such that at least the distal end of the cannula 135 passes at least partially through both septums when the receiver device 115 is coupled to the transfer device 110, as described in more detail below with reference to FIG. 12. At least one of the functions of both septums 160a and 160b is to wipe the cannula as the cannula withdraws in the proximal direction out of the receiver device 115. The second septum 160b provides a first wipe to the cannula as the cannula withdraws and the first septum 160a provides a second wipe. The air space 1110 acts as a repository for any fluid that passes through the second septum 160b during withdrawal of the cannula from the receiver device 110.

The structural configurations of the septums can vary. For example, the septums 160a and 160b can be manufactured of separate pieces of material, as shown in FIGS. 11 and 12 such that two separate, distinct septums are used. In another embodiment, the septums 160a and 160b are connected to one another along at least a portion of the septums with the air gap 1110 still being interposed between the two septums. Thus, the two septums 160a and 160b can be formed from a single piece of material or multiple pieces of material. In yet another embodiment, one or both of the septums is replaced by a wiping member that can be any structure or device configured to wipe the cannula during withdrawal of the cannula. For example, one or both of the septums can be replaced by a duckbill-type valve or seal that wipes the cannula. Other types of structures can be used as long as the structure provides two separate wipes and an air space 1110 therebetween.

In use, the transfer device 110 is coupled to the receiver device 115 in the manner described above with respect to the previous embodiments. As the transfer device 110 is coupled to the receiver device 115, the distal end of the cannula 135 first passes through the first septum 160a and then passes through the second septum 160b. The distal end of the cannula 135 then communicates with the passageway 155 in the receiver device 115, as shown in FIG. 12. Fluid can then be transferred between the transfer device 110 and the receiver device 115 via the cannula 135.

The transfer device 110 can then be de-coupled from the receiver device 115 such that the cannula 135 withdraws in a distal direction out of the receiver device 115. As this occurs, the distal end of the cannula 135 first passes through the second septum 160b, which wipes the cannula 135 during withdrawal of the cannula 135. It might be possible for some fluid to escape out of the passageway 155 through the second septum 160b. If this occurs, such escaped fluid is advantageously trapped within the air space 1110 that is positioned between the two septums 160a, 160b. As the cannula 135 continues to withdraw from the receiver device 115, the cannula 135 next passes through the first septum 160a, which provides a second wipe to the cannula 135. In this manner, the device shown in FIGS. 11 and 12 provide additional wiping of the cannula 135.

Although embodiments of various methods and devices are described herein in detail with reference to certain versions, it should be appreciated that other versions, embodiments, methods of use, and combinations thereof are also possible. Therefore the spirit and scope of the invention should not be limited to the description of the embodiments contained herein.

What is claimed:

1. A medical substance transfer system, comprising:
   (a) a transfer device including:
      (1) a transfer housing defining an interior chamber;
      (2) a first septum movably disposed in a distal end of the chamber in a sealing relationship with the chamber, the first septum having a distal surface flush with a distal edge of the transfer housing when the transfer device and receiver device are uncoupled from one another;
      (3) a cannula extending through the chamber, and wherein, when the transfer device is uncoupled from the receiver device, a distal tip of the cannula is positioned proximal of the distal edge of the transfer housing;
      (4) a biasing member inside the chamber, the biasing member adapted to bias the first septum toward the distal end of the chamber; and
   (b) a receiver device adapted to removably couple to the transfer device, the receiver device including:
      (1) a receiver housing defining an interior passageway, wherein the interior passageway is in communication with a distal tip of the cannula when the transfer device and receiver device are coupled to one another;
      (2) a second septum disposed in a proximal region of the receiver housing, the second septum having a proximal surface flush with a proximal edge of the entire receiver device when the transfer device and receiver device are uncoupled from one another, wherein the proximal surface of the second septum is in juxtaposed contact with the distal surface of the first septum when the transfer device and receiver device are coupled to one another and wherein the second septum provides a barrier to prevent fluid from escaping from the interior passageway of the receiver housing;
   wherein at least a portion of the receiver housing inserts inside the transfer housing when the receiver housing and the transfer housing are coupled to one another, and wherein at least a portion of the first septum moves in a proximal direction through the interior chamber of transfer housing during coupling of the receiver device to the transfer device, and wherein the first septum maintains a sealed relationship with an interior wall of the chamber during such movement.

2. A system as in claim 1, wherein the first and second septums contact the cannula when the transfer device and receiver device are coupled to one another.

3. A system as in claim 1, wherein a distal tip of the cannula is at all times positioned inside the chamber of the transfer housing and proximal of the distal end of the transfer housing when the transfer device and receiver device are uncoupled from one another.

4. A system as in claim 1, wherein the distal tip cannula is at least partially positioned inside the first septum when the transfer device and receiver device are uncoupled from one another.

5. A system as in claim 1, wherein the first and second septums have slits for passage of the cannula therethrough, and wherein the first and second septums comprise resilient material that provides bulk resilience to maintain a closed, default state of the slits.

6. A system as in claim 1, wherein the cannula has a blunt distal tip.

7. A system as in claim 1, wherein the transfer device attaches to a first vessel such that the cannula fluidly communicates with the first vessel, and wherein the receiver device attaches to a second vessel such that the interior passageway of the receiver housing communicates with the second vessel, and wherein upon connection of the transfer device to the receiver device the cannula and interior passageway collectively provide a passageway between the first and second vessels.

8. A system as in claim 1, wherein the first septum and the biasing member are separate devices.

9. A system as in claim 1, wherein the distal surface of the first septum is flat.

10. A system as in claim 1, wherein the proximal surface of the second septum is flat.

11. A system as in claim 1, wherein the receiver device further includes a third septum inside the receiver housing distal of the second septum, and wherein an air space is interposed between the second and third septums inside the receiver housing and such that at least a distal end of the cannula passes at least partially through the second and third septums when the receiver device couples to the transfer device.

* * * * *

UNITED STATES PATENT AND TRADEMARK OFFICE
CERTIFICATE OF CORRECTION

PATENT NO. : 7,648,491 B2
APPLICATION NO. : 11/435274
DATED : January 19, 2010
INVENTOR(S) : Bob Rogers It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this

Twenty-third Day of November, 2010

David J. Kappos
*Director of the United States Patent and Trademark Office*